United States Patent
Robinson

[11] Patent Number: 5,560,816
[45] Date of Patent: Oct. 1, 1996

[54] METHOD FOR ELECTROLYZING FLUIDS

[75] Inventor: Daniel L. Robinson, Salt Lake City, Utah

[73] Assignee: Medical Discoveries, Inc., Logan, Utah

[21] Appl. No.: 602,317

[22] Filed: Feb. 16, 1996

Related U.S. Application Data

[62] Division of Ser. No. 296,970, Aug. 26, 1994, Pat. No. 5,507,932.

[51] Int. Cl.$^6$ .......................... C25B 15/08; A61M 35/00
[52] U.S. Cl. ........................................... 205/687; 604/290
[58] Field of Search .................................. 205/687, 621,
205/622, 625, 626, 530, 630–632, 637–639;
604/290

[56] References Cited

U.S. PATENT DOCUMENTS

| | | | |
|---|---|---|---|
| 998,982 | 7/1911 | Pier | 205/621 X |
| 4,010,085 | 3/1977 | Carlin | 205/621 |
| 4,236,992 | 12/1980 | Themy | 205/625 |
| 4,938,854 | 7/1990 | Sharifian et al. | 205/687 |

*Primary Examiner*—Donald R. Valentine
*Attorney, Agent, or Firm*—Thorpe, North, & Western, L.L.P.

[57] ABSTRACT

An apparatus for electrolyzing fluids is disclosed. The resulting electrolyzed fluids are particularly suited for treating physiological materials such as whole blood, plasma, or cell isolates in order to reduce the effect of harmful microorganisms. A container holds the fluid and a power supply provides a source of electrical current to an anode and a cathode positioned within the container. The anode comprises a base material selected from titanium and niobium. An outer layer of platinum is bonded to the base. The anode comprises a cylindrical shape. The cathode is also connected to the power supply and comprises titanium and has a substantially cylindrical shape. The cathode is positioned concentrically in relation to the anode. The spacing between the cathode and the anode is not greater than a preferred amount. Moreover, the voltage potential between the cathode and the anode is not greater than a preferred amount.

21 Claims, 4 Drawing Sheets

METHOD FOR ELECTROLYZING FLUIDS

This application is a divisional of U.S. patent application Ser. No. 08/296,970 filed on Aug. 26, 1994 now U.S. Pat. No. 5,507,932

BACKGROUND

1. The Field of the Invention

This invention relates to apparatus and methods for electrolyzing fluids and more particularly relates to apparatus and methods for electrolyzing saline solutions for use in medical treatments.

2. The Prior Art

It has long been known that the electrolysis of fluids can result in useful products. In particular, the electrolysis of saline solution results in the production of chlorine and ozone. It is known that the products resulting from the electrolysis of saline solutions are in vitro microbicides for hard surfaces. Thus, various apparatus and methods have been proposed for electrolyzing saline solution, however, all of the previously available schemes present one or more drawbacks.

For example, U.S. Pat. Nos. 4,236,992 and 4,316,787 to Themy disclose an electrode, method and apparatus for electrolyzing dilute saline solutions to produce effective amounts of disinfecting agents such as chlorine, ozone and hydroxide ions. One apparatus for producing electrolyzed saline solutions was previously available under the trade name Ster-O-Lizer. Laboratory reports and other data available from testing of electrolyzed saline solutions from various Ster-O-Lizer models have shown that it is effective in keeping water free of pathogenic organisms. Tests conducted in vitro further show that certain microorganisms, inclusive of *Pseudomonas aeruginosa, Escherichia coli, Staphylococcus aureus, Candida albicans,* and *Salmonella typhi*, are non-infectious after exposure to electrolyzed saline solutions.

For many years, ozone ($O_3$) has been used for the treatment of viral infections. Chlorine, in the form of chlorinated lime, was used successfully as early as 1846 to prevent and fight puerperal fever. By 1911, the U.S. purified as much as 800,000,000 gallons of water through the chlorination process. Wide use of chlorine as a 0.05% sodium hypochlorite solution (Dakins Solution) for open and infected wounds began in 1915. Dakins Solution was a standard product up to 1963 listed in the British Pharmacopeia.

As reported by Wilk et al., *International Congress on Technology and Technology Exchange*, First Euro-American Symposium, Paris, France (1992) and *Science, Total Environment*, 63:191–197 (1987), certain combinations of ozone and chlorine have significantly greater activity than either used separately against a variety of bacteria including *Staphylococcus aureus* and *Pseudomonas aeruqinosa. Candida albicans* was also reported to be effectively killed by a combination of ozone and chlorine.

In view of the many uses of chlorine and ozone, numerous apparatus and methods have been proposed for generating chlorine and ozone. Significantly, the previously available apparatus and methods have not been well-suited to producing electrolyzed saline containing finite amounts of ozone and chlorine for treatment of physiological fluids for the destruction of microbes in warm blooded animals. It has recently been discovered that there are situations where physiological fluids can be beneficially treated using electrolyzed saline solutions. The treatment of physiological fluids such as whole blood, plasma or cell isolates by electrolyzed saline solution which renders them benign from infectious organisms without destroying the therapeutic characteristics of such fluids is now possible. Disadvantageously, the available apparatus and methods for generating chlorine and ozone are not well-suited for treatment of physiological fluids such as whole blood, plasma, or cell isolates.

Methods for treatment of physiological fluids using electrolyzed solutions are set forth in U.S. patent application Ser. No. 07/527,321 filed May 23, 1990 (now U.S. Pat. No. 5,334,383 issued Aug. 2, 1994) and 08/275,904 filed Jul. 15, 1994, all of which are now incorporated herein by reference in their entireties. In these documents, an electrolyzed saline solution, properly made and administered in vivo, is effective in the treatment of various infections brought on by invading antigens and particularly viral infections. Thus, it would be a great advance in the art to provide an apparatus and method for electrolyzing saline solution for administration in vivo.

BRIEF SUMMARY AND OBJECTS OF THE INVENTION

In view of the above described state of the art, the present invention seeks to realize the following objects and advantages.

It is an object of the present invention to provide an apparatus and method for electrolyzing saline solutions which are particularly suitable for administration in vivo.

It is also an object of the present invention to provide an apparatus and method for electrolyzing fluids which does not introduce harmful substances into the fluid.

It is a further object of the present invention to provide an apparatus and method for electrolyzing saline solutions which is reliable and can be economically operated.

These and other objects and advantages of the invention will become more fully apparent from the description and claims which follow, or may be learned by the practice of the invention.

The present invention provides and an apparatus for electrolyzing fluids. The resulting electrolyzed fluids, such as a saline solution, are particularly suited for treating physiological materials such as whole blood, plasma or cell isolates in order to reduce the effect of harmful microorganisms.

A preferred embodiment of the present invention includes a container means for holding a fluid which is to be electrolyzed. A power supply means provides a source of electrical current. At least a first anode and a second anode are connected to the power supply means. The anodes and cathodes are positioned within the container means so as to be immersed in the fluid to be electrolyzed.

The anode comprises a base metal. The base metal is a metal selected from the group consisting of titanium and niobium. An outer layer of platinum is bonded to the base. The anode comprises a cylindrical shape.

The cathode is also connected to the power supply means. The cathode preferably comprises titanium or niobium and also has a substantially cylindrical shape. The cathode is positioned concentrically in relation to the anode. The spacing between the cathode and the anode is not greater than a preferred amount. Moreover the voltage potential between the cathode and the anode is not greater than a preferred amount.

BRIEF DESCRIPTION OF THE DRAWINGS

In order to better appreciate how the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

Figure 1:
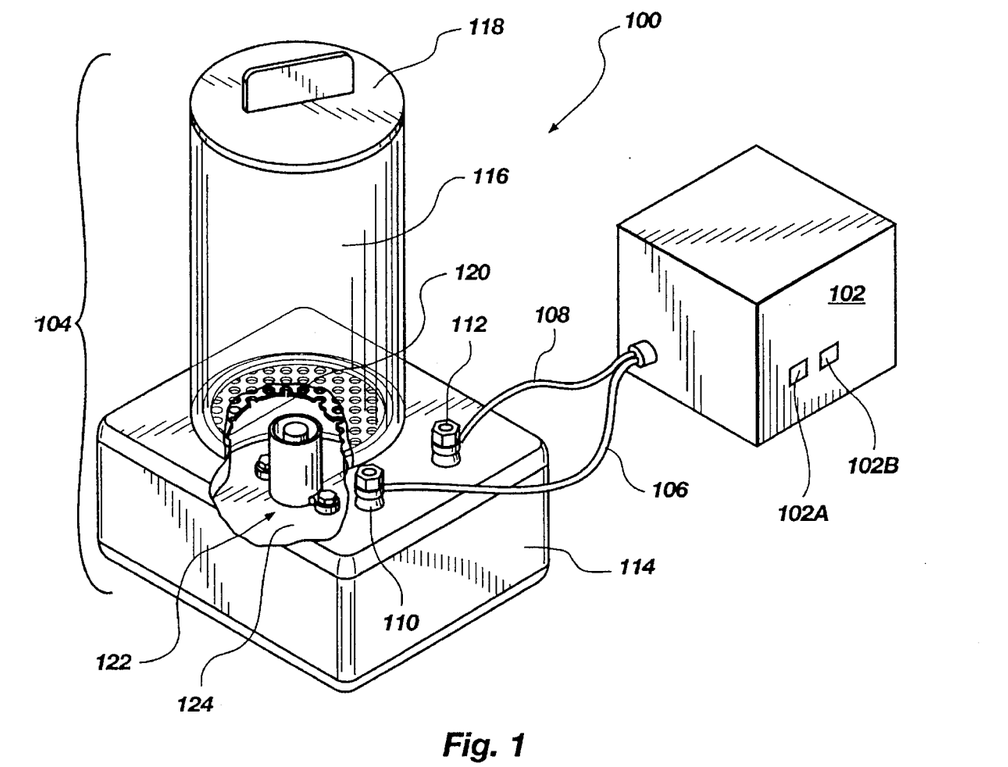
FIG. 1 is a perspective view of a first presently preferred embodiment of the present invention.

Referring first to FIG. 1, which is a perspective view of a first presently preferred embodiment of the present invention generally represented at 100, includes a power supply 102 and a fluid receptacle represented at 104. The fluid receptacle 104 includes a base 114 upon which is attached a fluid vessel 116. The base 114 can preferably be fabricated from an insulative plastic material. The fluid vessel 116 is preferably fabricated from an inert clear plastic material which is compatible with biological processes as available in the art.

A lid 118 is provided to cover the fluid vessel 116 and keep contaminants out of the fluid vessel 116. A screen 120 is positioned to prevent foreign objects, which might accidentally fall into the fluid vessel 116, from falling to the bottom of the fluid vessel 116. The saline solution which is to be treated is placed into the fluid vessel 116, and the lid 118 placed, for the necessary period of time after which the electrolyzed saline solution can be withdrawn from the fluid vessel 116, for example into a syringe, for use. The fluid vessel 116 is sealed at its bottom by a floor 124 which is attached to the interior of the base 114.

An electrode assembly, generally represented at 122, is attached to the floor 124 so that any fluid in the fluid vessel 116 is exposed to the electrode assembly 122. The electrode assembly 122 is electrically connected to the power supply 102 via terminals 110 and 112 and cables 106 and 108, respectively. The power supply 102 should deliver a controlled voltage and current to the electrode assembly 122 when fluid is placed into the fluid vessel 116. The voltage and current applied to the electrode assembly 122 will vary according to the fluid being electrolyzed. A control for setting and measuring the voltage 102A and a control for setting and measuring the current 102B is provided in the power supply. In accordance with the present invention, a low voltage of less than about 30 volts DC is used. Exemplary voltage and current values, and the advantages which accrue when using the preferred voltage and current values, will be explained shortly.

Figure 2:
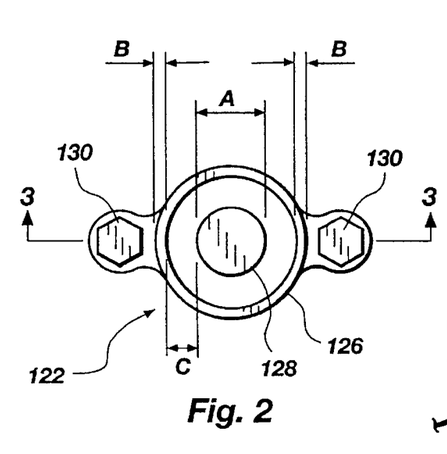
FIG. 2 is a detailed top view of the electrode assembly represented in FIG. 1.

FIG. 2 is a top view of the electrode assembly 122 represented in FIG. 1. The electrode assembly 122 preferably comprises a cylindrical inner electrode 128 and a cylindrical outer electrode 126. The inner electrode 128 is preferably solid or any hollow in the inner electrode is sealed so that fluid does not enter any such hollow. The cylindrical shape of the inner electrode 128 and the outer electrode 126 is preferred and results in better performance than obtained with electrodes of other shapes, e.g., elongated flat panels.

The diameter A of the inner electrode 128 is preferably about one-half inch but the diameter A of the inner electrode can be selected by those skilled in the art in accordance with the particular application for the electrode using the information contained herein. The outer electrode 126 should be of a generally cylindrical shape and preferably be fabricated from titanium or niobium having a thickness (indicated at B in FIG. 2) which ensures that the inner electrode is shielded from potentially physical damage. As will be appreciated, titanium and niobium provide the advantage of resistance against corrosion which further prevents the introduction of harmful substances into the fluid being electrolyzed.

Still referring to FIG. 2, the space, indicated at C, between the inner electrode 128 and the outer electrode 126 does not exceed a maximum value. In contrast to previously available devices which separate the electrodes by greater distances and then utilize higher voltages to obtain the desired electrolyzation, the present invention keeps the electrode spacing small and obtains improved performance over other schemes. It is preferred that the space between the inner electrode 128 and the outer electrode 126 be not more than about one-half (½) inch; it is more preferred that the space between the inner electrode 128 and the outer electrode 126 be not more than about three-eights (⅜) inch; and, it is most preferred that the space between the inner electrode 128 and the outer electrode 126 be not more than about one-quarter (¼) inch.

Figure 3:
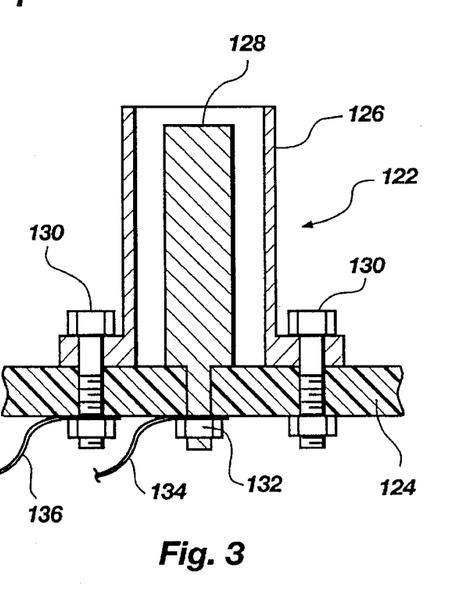
FIG. 3 is a side cross sectional view of the electrode assembly taken along line 3—3 in FIG. 2.

Reference will next be made to FIG. 3 which is a side cross sectional view of the electrode assembly taken along line 3—3 in FIG. 2. As seen in FIG. 3, the outer electrode 126 extends above the inner electrode 128 to provide improved electrical performance and physical protection. The outer electrode 126 is attached to the floor 124 by way of bolts 130, which extend through bores provided in the floor 124, and accompanying nuts. An electrical connection is made to the outer electrode 126 by a lead 136 attached to the bolt and nut. The lead 136 is attached to one of the terminals 110 or 112. Similarly, an electrical connection is made to the inner electrode 128 by a lead 134 which is held in place by a nut attached to a threaded stud extending from the bottom of the inner electrode and through a bore provided in the floor 124. The lead 134 is attached to the remaining one of the terminals 110 or 112. The leads 134 and 136 are kept insulated from any fluid which is present in the fluid vessel 116.

It is preferred that the inner electrode 128 function as the anode while the outer electrode function as the cathode when electrolyzing fluids and the power supply 102 and the terminals 110 and 112 should be properly arranged to carry this out.

It is recognized in the art that the anode is subject to destructive forces during electrolysis. In the prior art, the anode of an electrode assembly may dissolve to the point of being inoperative and may need to be replaced very often.

Critically, as the anode of an electrode assembly dissolves, the metallic components of the anode are dispersed into the fluid. If the fluid is a saline solution which will be used to treat physiological fluids, toxic substances dispersed into the solution, such as the materials comprising the anode, may be harmful or dangerous to the person who expects to be benefitted from the treatment.

Of all the possible materials for fabrication of the anode, the art recognizes that platinum is the least likely to be dissolved when used as an anode. Unfortunately, the cost of platinum precludes the use of an anode which consists entirely of platinum. Thus, it is common in the art to utilize another metal as a base for the anode with a layer of platinum being placed on surfaces which contact the fluid to be electrolyzed.

The present invention advantageously utilizes an inner electrode 128, i.e., an anode, which includes a base of titanium, and even more preferably niobium (also known as columbium), upon which a layer of platinum is provided wherever fluid contacts the anode. Significantly, niobium is a relatively good electrical conductor having a conductivity which is about three times greater than the conductivity of titanium. Moreover, if the base metal is exposed to the fluid, such as if a pinhole defect develops, toxic products are not produced by the contact between niobium and the fluid. Moreover, the high breakdown voltage in saline solution of the oxide which forms when a niobium base receives a layer of platinum provides further advantages of the present invention.

Upon a base of niobium, a layer of platinum is formed on the anode. The layer of platinum is preferably formed using a technique referred to in the art as brush electrodeposition which can be carried out by those skilled in the art using the information set forth herein. Other techniques can also be used to form the platinum layer, such as tank (immersion) electrodeposition, vapor deposition, and roll bonding, but brush electrodeposition is preferred because of its superior adhesion and resulting less porosity than other economically comparable techniques.

The thickness of the platinum layer is preferably greater than about 0.02 mils and is most preferably greater than about 0.06 mils, and up to about 0.20 mils. The combination of using niobium as a base for the anode of the electrode assembly and utilizing brush electrodeposition provides that the platinum layer can be much thinner than otherwise possible and still provide economical and reliable operation. It will be appreciated by those skilled in the art, that even with an anode fabricated in accordance with the present invention replacement of the anode, which preferably comprises the inner electrode 128 represented in FIG. 3, may be necessary after a period of use. The construction of the embodiments of the present invention facilitate replacement of the inner electrode 128 and the outer electrode 126 when it becomes necessary.

Figure 4:
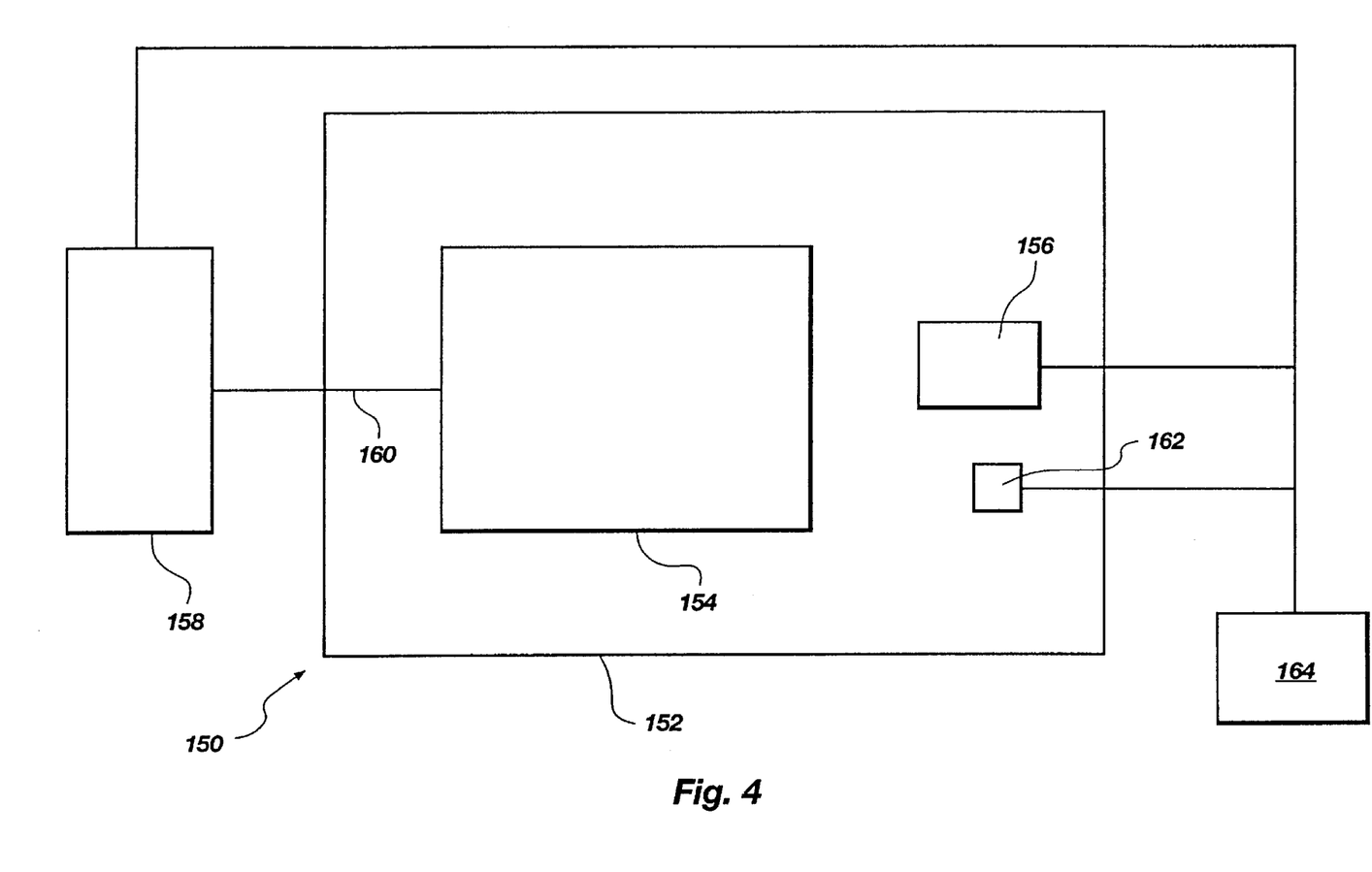
FIG. 4 is a block diagram of a second presently preferred embodiment of the present invention.

Represented in FIG. 4 is a block diagram of a second presently preferred embodiment, generally represented at 150, of the present invention. The embodiment represented in FIG. 4 is particularly adapted for treating large quantities of saline solution. Represented in FIG. 4 is a tank 152 in which the saline solution is electrolyzed. An electrode assembly 154 is provided in the tank and is preferably immersed into the solution. A power supply 158, capable of providing sufficient current at the proper voltage, is connected to the electrode assembly via a cable 160.

Also represented in FIG. 4 is a circulation device 156 which optionally functions to circulate the solution within the tank 152. A sensor 162 is also optionally provided to measure the progress of the electrolyzation of the solution in the tank 152, for example by measuring the pH of the solution. The sensor may preferably be an ion selective electrode which can be chosen from those available in the art. Other sensors, for example chlorine, ozone, and temperature sensors, may also be included within the scope of the present invention. A control unit 164 is optionally provided to coordinate the operation of the power supply 158, the circulation device 156, and the sensor 162 in order to obtain the most efficient operation of the apparatus 150.

It will be appreciated that devices such as power supply 158, circulation device 158, sensor 162, and control unit 164 can be readily obtained from sources in the industry and adapted for use with embodiments of the present invention by those skilled in the art using the information contained herein. In particular, the control unit 164 is preferably a digital microprocessor based device accompanied by appropriate interfaces all allowing for accurate control of the operation of the apparatus 150. It is also within the scope of the present invention to include structures to prevent contamination of the treated solution by contact with nonsterile surfaces and by airborne pathogens both during treatment and while the fluid is being transferred to the apparatus and being withdrawn from the apparatus.

Figure 5:
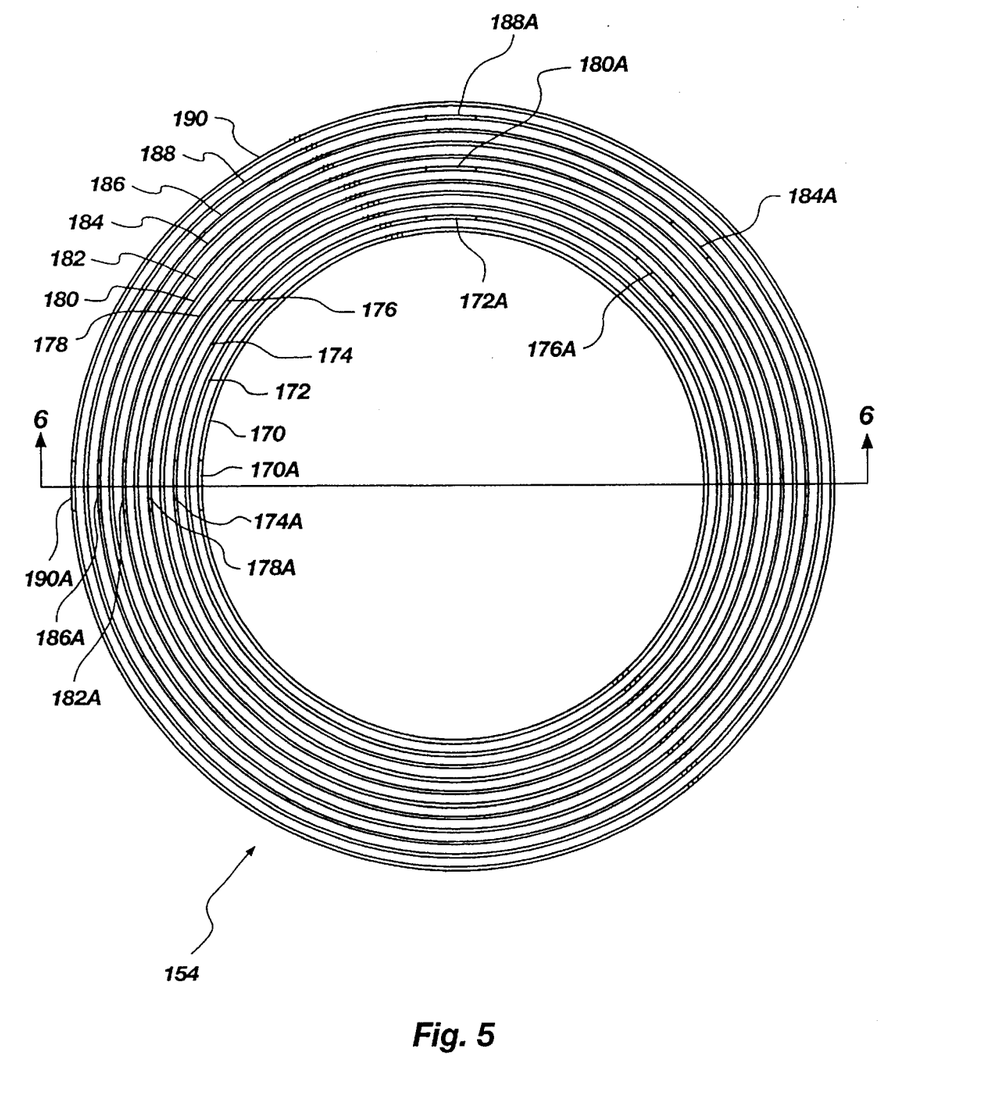
FIG. 5 is a top view of an electrode assembly preferred for use in the apparatus represented in FIG. 4.
Figure 6:
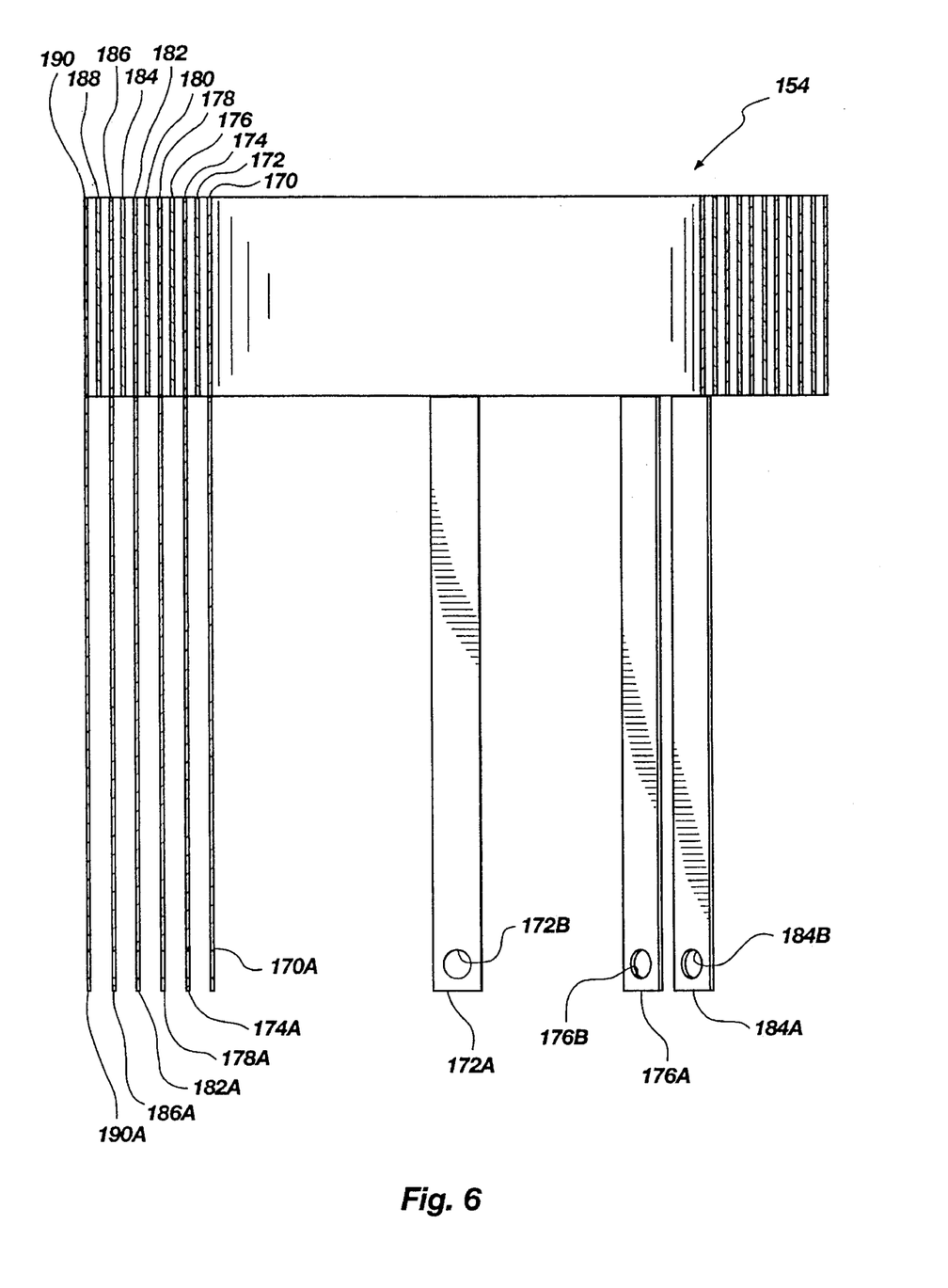
FIG. 6 is a cross sectional view taken along line 6—6 of FIG. 5.

Reference will next be made to FIGS. 5 and 6 which are a top view and cross sectional view, respectively, of an electrode assembly, generally represented at 154, which is preferred for use in the apparatus represented in FIG. 4. As can be seen best in FIG. 5, the electrode assembly 154 includes a plurality of concentrically arranged anodes and cathodes. The cylindrical shape and concentric arrangement of the electrodes represented in FIG. 5 provides for the most efficient operation. The number of electrodes which are included can be selected according to the application of the apparatus. For example, the number of electrodes may be six, seven, eight, the eleven represented in FIGS. 5 and 6, or more.

In FIG. 5, electrodes 170, 174, 178, 182, 186, and 190 preferably function as cathodes and are preferably fabricated in accordance with the principles set forth above in connection with the outer electrode represented at 126 in FIGS. 1–3. Furthermore, in FIG. 5 electrodes 172, 176, 180, 184, and 188 function as anodes and are preferably fabricated in accordance with the principles set forth above in connection with the inner electrode represented at 128 in FIGS. 1–3.

In the cross sectional side view of FIG. 6 a plurality of tabs extend from the cylindrical electrodes 170, 172, 174, 176, 178, 180, 182, 184, 186, and 190 to facilitate making an electrical connection thereto. Provided below in Table A are the relationship between the tabs illustrated in FIG. 6 and the electrodes.

TABLE A

| Electrode | Tab | Function |
| --- | --- | --- |
| 170 | 170A | Cathode |
| 172 | 172A | Anode |
| 174 | 174A | Cathode |
| 176 | 176A | Anode |
| 178 | 178A | Cathode |
| 180 | 180A (Not illustrated in FIG. 6) | Anode |
| 182 | 182A | Cathode |
| 184 | 184A | Anode |

TABLE A-continued

| Electrode | Tab | Function |
| --- | --- | --- |
| 186 | 186A | Cathode |
| 188 | 188A (Not illustrated in FIG. 6) | Anode |
| 190 | 190A | Cathode |

Using the tabs 170A, 172A, 174A, 176A, 178A, 180A, 182A, 184A, 186A, 188A, and 190A, those skilled in the art can provide the necessary electrical connections to the electrodes 170, 172, 174, 176, 178, 180, 182, 184, 186, and 190 and can also provide numerous structures to prevent contact between the tabs and the fluid to be treated. Each of the tabs illustrated in FIG. 6 are provided with an aperture, such as those represented at 172B, 176B, and 184B, which receive a wiring connector.

While the apparatus described herein has many uses, the most preferred use of the apparatus described herein is subjecting sterile saline solution to electrolysis. The electrolyzed saline solution can then be used to treat a patient. The saline solution preferably has an initial concentration in the range from about 0.25% to about 1.0% NaCl which is about one-fourth to full strength of normal or isotonic saline solution. According to *Taber's Cyclopedic Medical Dictionary*, E. A. Davis, Co. 1985 Ed., an "isotonic saline" is defined as a 0.16 M NaCl solution or one containing approximately 0.95% NaCl; a "physiological salt solution" is defined as a sterile solution containing 0.85% NaCl and is considered isotonic to body fluids and a "normal saline solution;" a 0.9% NaCl solution which is considered isotonic to the body. Therefore, the terms "isotonic," "normal saline," "balanced saline," or "physiological fluid" are considered to be a saline solution containing in the range from about 0.85% to about 0.95% NaCl. Moreover, in accordance with the present invention, a saline solution may be subjected to electrolysis at concentrations in the range from about 0.15% to about 1.0%.

It is preferred that one of the above described saline solutions be diluted with sterile distilled water to the desired concentration, preferably in the range from about 0.15% to about 0.35% prior to treatment in accordance with the present invention. This dilute saline solution is subjected to electrolysis using the embodiments of the present invention at a voltage, current, and time to produce an appropriately electrolyzed solution as will be described shortly. It is presently preferred to carry out the electrolysis reaction at ambient temperatures.

The voltage and current values provided herein are merely exemplary and the voltage and current values which are used, and the time the saline solution is subject to electrolysis, is determined by many variables, e.g., the surface area and efficiency of the particular electrode assembly and the volume and/or concentration of saline solution being electrolyzed. For electrode assemblies having a different surface area, greater volumes of saline solution, or higher concentrations of saline solutions the voltage, current, or time may be higher and/or longer than those exemplary values provided herein. In accordance with the present invention, it is the generation of the desired concentration of ozone and active chlorine species which is important. Electrolyzation of the saline solution also results in other products of the electrolysis reaction including members selected from the group consisting of hydrogen, sodium and hydroxide ions. It will be appreciated that the interaction of the electrolysis products results in a solution containing bioactive atoms, radicals or ions selected from the group consisting of chlorine, ozone, hydroxide, hypochlorous acid, hypochlorite, peroxide, oxygen and perhaps others along with corresponding amounts of molecular hydrogen and sodium and hydrogen ions.

According to Faraday's laws of electrolysis, the amount of chemical change produced by a current is proportional to the quantity of electrons passed through the material. Also, the amounts of different substances liberated by a given quantity of electrons are proportional to the chemical equivalent weights of those substances. Therefore, to generate an electrolyzed saline having the desired concentrations of ozone and active chlorine species from saline solutions having a saline concentration of less than about 1.0%, voltage, current, and time parameters appropriate to the electrodes and solution are required to produce an electrolyzed solution containing in the range from about 5 to about 100 mg/L of ozone and a free chlorine content in the range from about 5 to about 300 ppm. For in vitro use these solutions can be utilized without further modification or they can be adjusted as desired with saline or other solutions. Prior to in vivo use, the resulting solution may be adjusted or balanced to an isotonic saline concentration with sufficient hypertonic saline, e.g., 5% hypertonic saline solution.

In general, the electrolyzed solutions produced using the apparatus described herein, which are referred to as microbicidal solutions, will have an ozone content in the range from about 5 to about 100 mg/L and an active chlorine species content in the range from about 5 to about 300 ppm. More preferably the ozone content will be in the range from about 5 to about 30 mg/L and the active chlorine species content will be in the range from about 10 to about 100 ppm. Most preferably the ozone content will be in the range from about 9 to about 15 mg/L and the active species content will be in the range from about 10 to about 80 ppm. By active chlorine species is meant the total chlorine concentration attributable to chlorine content detectable by a chlorine ion selective electrode and will be selected from the group consisting of chlorine, hypochlorous acid and hypochlorite ions or moieties.

The pH of the solution is preferably in the range from about 7.2 to about 7.6 and, when used for intravenous administration, most preferably in the range from about 7.35 to about 7.45 which is the pH range of human blood. An effective amount of the resulting balanced microbicidal saline solution is administered by appropriate modes, e.g., intravenously, orally, vaginally or rectally and may vary greatly according to the mode of administration, condition being treated, the size of the warm-blooded animal, etc.

Particular dosages and methods of administration, as well as additional components to be administered, can be determined by those skilled in the art using the information set forth herein and set forth in the U.S. patent documents previously incorporated herein by reference. As explained in the cited U.S. patent documents, although it is known that electrolyzed saline solutions possess in vitro microbicidal activity it has long been thought that components in the electrolyzed solution, such as ozone and chlorine, are toxic to warm blooded animals and should not be utilized for in vivo purposes. It has now been found, however, that saline solutions, which have been subjected to electrolysis to produce finite amounts of ozone and active chlorine products, can be injected into the vascular system to create a reaction to assist in the removal, passivation, or destruction of a toxin.

In order to arrive at the preferred end product, electrolyzed saline solution using the apparatus illustrated in FIGS. 1–3, about a 0.33% (about one third physiologically normal) saline solution is placed in the fluid vessel 116 (FIG. 1) and the apparatus is operated for about 5 to 15 minutes with a voltage between the electrodes being maintained in the range from about 10 volts to about 20 volts with a current flow maintained in the range from about 5 to about 20 amps.

As one example of the use of the embodiment of FIGS. 1–3, a 0.225% saline solution is subjected to a current of 3 amperes at 20 volts (DC) for a period of three minutes. A 17 ml portion of this electrolyzed solution is aseptically diluted with 3 mls of a sterile 5% saline resulting in a finished isotonic electrolyzed saline having an active ozone content of 12±2 mg/L and an active chlorine species content of 60±4 ppm at a pH of 7.4.

It will be appreciated that the low voltages used in accordance with the present invention are preferably not greater than forty (40) volts DC or an equivalent value if other than direct current is used. More preferably, the voltages used in accordance with the present invention is not more than about thirty (30) volts DC. The use of low voltages avoids the problem of production of undesirable products in the fluid which can result when higher voltages are used. In accordance with the present invention, the close spacing of the electrodes facilitates the use of low voltages.

In another example, to show that the embodiment of FIGS. 1–3 can be used to effectively carry out electrolysis in saline solutions up to about 1% in concentration, the electrolysis reaction is carried out at saline concentrations of 0.3, 0.6 and 0.9%, respectively. The active chlorine species ($Cl_2$) and ozone ($O_3$) contents were measured and are provided in Table B.

TABLE B $Cl_2$ and $O_3$ Content from salines at Varying Concentrations

| Saline Concentration (% NaCl) | $Cl_2$ Concentration (ppm) | $O_3$ Concentration (mg/mL) |
| --- | --- | --- |
| 0.3 | 129 | 21.8 |
| 0.6 | 161 | 26.6 |
| 0.9 | 168 | 28.0 |

As can be seen from Table B, the resulting electrolyzed saline solution includes active components which are within the parameters required for effective treatment.

It will be appreciated that the features of the present invention, including the close electrode spacing, the low voltages used, and the materials used to fabricate the electrodes, result in an apparatus which provides unexpectedly better results than the previously available devices and schemes.

From the foregoing, it will be appreciated that the present invention provides an apparatus and method for electrolyzing saline solutions which are particularly suitable for administration in vivo and which does not introduce harmful substances into the electrolyzed fluid. The present invention also provides an apparatus and method for electrolyzing saline solutions which is reliable and can be economically operated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of electrolyzing saline solution for use as an in vivo treatment for a human, the method comprising the steps of:

placing the saline solution in a container, the saline solution having a saline concentration of at least about 0.15% and the container means comprising a container fabricated from a biologically compatible material;

providing a first anode in the container, the anode comprising a base, said base comprising a metal selected from the group consisting of platinum, titanium and niobium, said first anode further comprising an outer layer of platinum bonded to the base, the anode comprising a cylindrical shape;

connecting the first anode to a power supply;

providing a first cathode in the container, the cathode comprising a metal and being substantially cylindrical in shape and positioned concentrically in relation to the anode, the spacing between the cathode and the anode being not greater than about one-half inch;

connecting the first cathode to the power supply;

applying a voltage potential between the first cathode and the first anode which is less than about thirty volts; and withdrawing the saline solution from the container and administering it to a human.

2. A method for electrolyzing fluids as defined in claim 1 further comprising:

providing a second anode in the container connected to the power supply; and a second cathode connected to the power supply, the spacing between the second cathode and the second anode being not greater than about three-eights inch.

3. A method for electrolyzing fluids as defined in claim 1 further comprising:

providing a plurality of anodes each connected to the power supply; and a plurality of cathodes each connected to the power supply, the spacing between each of the plurality of cathodes and the plurality of anodes being not greater than about three-eights inch.

4. A method for electrolyzing fluids as defined in claim 1 wherein the first anode consists of a base metal and an outer layer, the base metal consisting essentially of niobium and the outer layer consisting essentially of platinum and wherein the first cathode consists essentially of titanium.

5. A method for electrolyzing fluids as defined in claim 1 wherein the first anode consists of a base metal and an outer layer, the base metal consisting essentially of niobium and the outer layer consisting essentially of platinum and wherein the first cathode consists essentially of niobium.

6. A method for electrolyzing fluids as defined in claim 1 wherein the container further comprises a lid.

7. A method for electrolyzing fluids as defined in claim 1 wherein the container comprises a cylindrical container comprising a top portion and a bottom portion and wherein the first anode and the first cathode are positioned in the bottom portion of the container.

8. A method for electrolyzing fluids as defined in claim 1 wherein the base consists essentially of niobium.

9. A method for electrolyzing fluids as defined in claim 1 wherein the base consists essentially of titanium.

10. A method for electrolyzing fluids as defined in claim 1 wherein the first anode comprises an anode surface and the first cathode comprises a cathode surface and the anode surface and the cathode surface are substantially parallel.

11. A method for electrolyzing fluids as defined in claim 1 wherein the outer layer of platinum comprises a layer of platinum having a thickness in the range from about 0.02 mils to about 0.20 mils.

12. A method for electrolyzing fluids as defined in claim 1 wherein the outer layer of platinum comprises a layer of platinum having a thickness of about 0.06 mils.

13. A method for electrolyzing fluids as defined in claim 1 wherein the spacing between the cathode and the anode is not greater than about one-quarter inch.

14. A method of electrolyzing saline solution for use as a treatment for a human, the method comprising the steps of:

providing a first anode in the container, the anode comprising a cylindrical shape;

connecting the first anode to a power supply;

providing a first cathode in the container, the cathode comprising a metal and being substantially cylindrical in shape and positioned substantially concentrically in relation to the anode;

connecting the first cathode to the power supply;

applying a voltage potential between the first cathode and the first anode which is less than about thirty volts; and withdrawing the saline solution from the container and administering it to a human.

15. A method for electrolyzing fluids as defined in claim 14 further comprising:

providing a second anode in the container connected to the power supply; and a second cathode connected to the power supply, the spacing between the second cathode and the second anode being not greater than about one-half inch.

16. A method for electrolyzing fluids as defined in claim 14 further comprising:

providing a plurality of anodes each connected to the power supply; and a plurality of cathodes each connected to the power supply, the spacing between each of the plurality of cathodes and the plurality of anodes being not greater than about three-eights inch and the voltage potential between each of the plurality of cathodes.

17. A method for electrolyzing fluids as defined in claim 14 wherein the first anode consists of a base metal and an outer layer, the base metal consisting essentially of niobium and the outer layer consisting essentially of platinum and wherein the first cathode consists essentially of niobium.

18. A method for electrolyzing fluids as defined in claim 14 wherein the container further comprises a lid.

19. A method for electrolyzing fluids as defined in claim 14 wherein the container comprises a cylindrical container comprising a top portion and a bottom portion and wherein the first anode and the first cathode are positioned in the bottom portion of the container.

20. A method for electrolyzing fluids as defined in claim 14 wherein the first anode comprises an anode surface and the first cathode comprises a cathode surface and the anode surface and the cathode surface are substantially parallel.

21. A method for electrolyzing fluids as defined in claim 14 wherein the spacing between the cathode and the anode is not greater than about one-quarter inch.

* * * * *